United States Patent
Wallin et al.

(10) Patent No.: US 8,610,066 B2
(45) Date of Patent: Dec. 17, 2013

(54) DEVICE FOR RADIATION ABSORPTION MEASUREMENTS AND METHOD FOR CALIBRATION THEREOF

(75) Inventors: Svante Wallin, Bjärred (SE); Leif Uneus, Kävlinge (SE)

(73) Assignee: Opsis AB, Furulund (SE)

( * ) Notice: Subject to any disclaimer, the term of this patent is extended or adjusted under 35 U.S.C. 154(b) by 0 days.

(21) Appl. No.: 13/502,950

(22) PCT Filed: Oct. 28, 2009

(86) PCT No.: PCT/EP2009/064227
§ 371 (c)(1),
(2), (4) Date: Apr. 19, 2012

(87) PCT Pub. No.: WO2011/050841
PCT Pub. Date: May 5, 2011

(65) Prior Publication Data
US 2012/0200844 A1    Aug. 9, 2012

(51) Int. Cl.
*G01J 5/00*    (2006.01)
(52) U.S. Cl.
USPC ....................................... 250/338.1
(58) Field of Classification Search
USPC ............... 250/338.1–338.5, 340, 342–352
See application file for complete search history.

(56) References Cited

U.S. PATENT DOCUMENTS

| | | | |
|---|---|---|---|
| 4,746,218 A * | 5/1988 | Lord, III | 356/437 |
| 5,184,017 A | 2/1993 | Tury et al. | |
| 5,255,073 A | 10/1993 | Wallin et al. | |
| 5,420,723 A | 5/1995 | Galle | |
| 5,498,872 A | 3/1996 | Stedman et al. | |
| 6,396,056 B1 * | 5/2002 | Lord et al. | 250/252.1 |
| 2004/0036027 A1 | 2/2004 | Horton et al. | |
| 2006/0237657 A1 | 10/2006 | Gamiles et al. | |
| 2007/0164220 A1 | 7/2007 | Luk | |

FOREIGN PATENT DOCUMENTS

| | | |
|---|---|---|
| EP | 0472637 B1 | 3/1992 |
| EP | 0703444 A1 | 3/1996 |
| WO | 9004761 | 5/1990 |

* cited by examiner

*Primary Examiner* — Kiho Kim
(74) *Attorney, Agent, or Firm* — Capitol City TechLaw

(57) ABSTRACT

A device for radiation absorption measurements may include a radiation source emitting electromagnetic radiation having a wavelength in the interval 0.2 μm-20 μm, a detector detecting the electromagnetic radiation, when in a measurement mode at least a portion of the radiation has passed through a medium and been reflected by a surface at a distance from the radiation source, before reaching the detector. The device may further include a fluid calibration cell, which is adapted to be arranged in the path of the electromagnetic radiation between the radiation source and the detector. A method for calibrating a device for radiation absorption measurements may involve emitting electromagnetic radiation having a wavelength in the interval 0.2 to 20 μm, directing at least a portion of the electromagnetic radiation through a fluid calibration cell, and detecting the electromagnetic radiation.

13 Claims, 3 Drawing Sheets

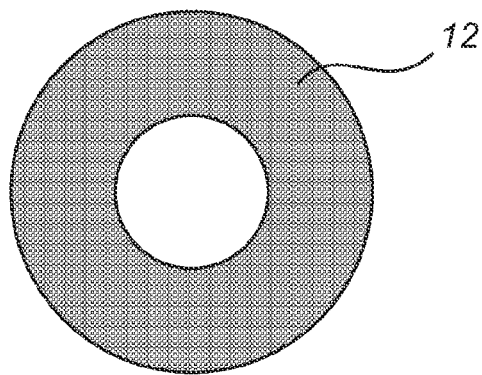
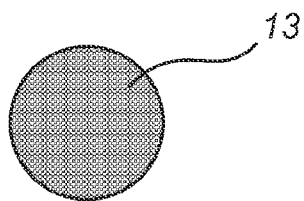
Fig. 2a   Fig. 2b
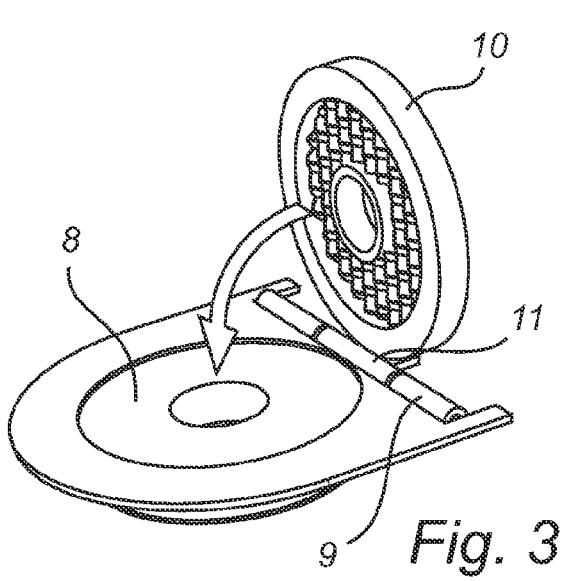
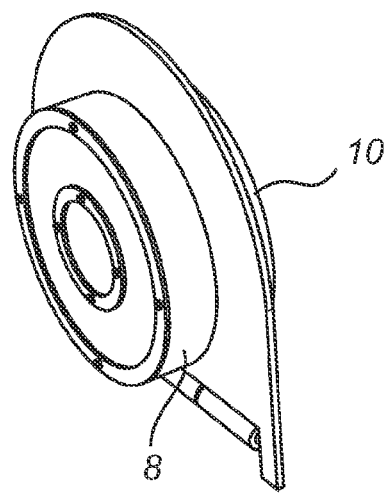
Fig. 3a   Fig. 3b
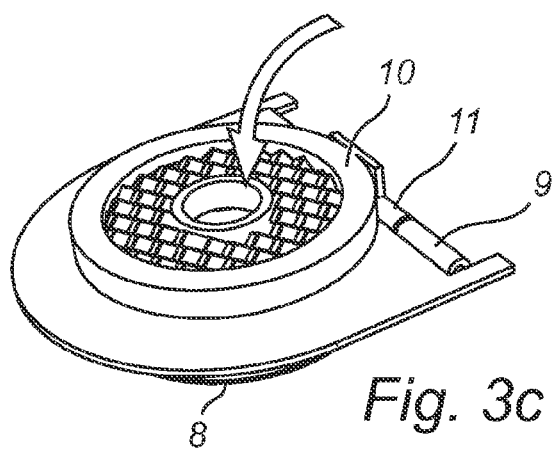
Fig. 3c

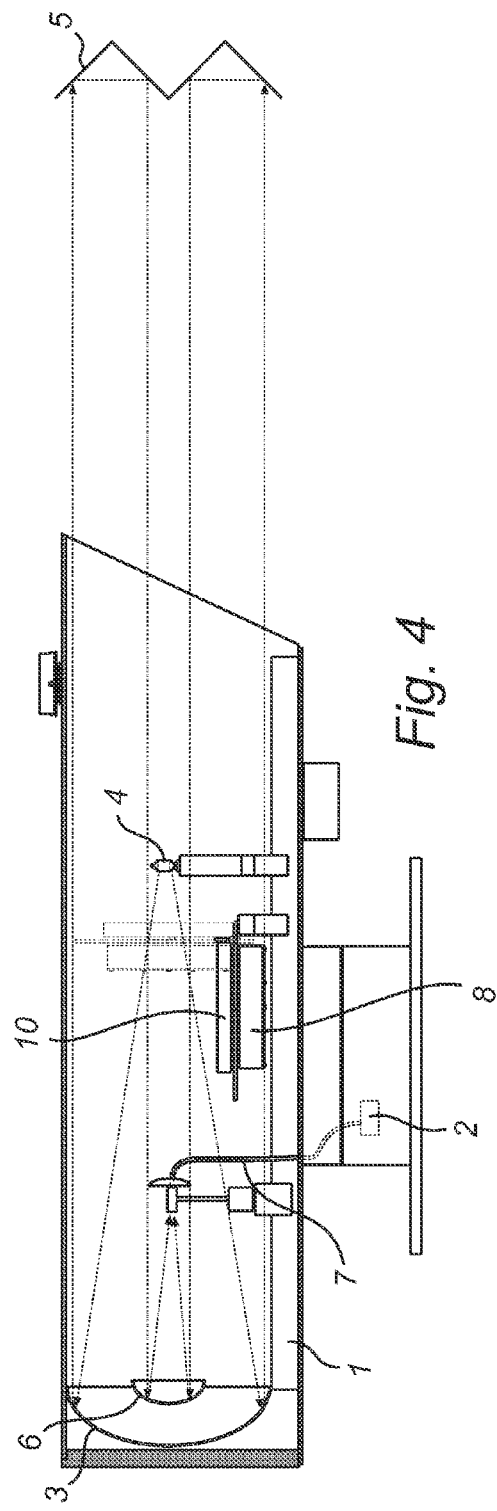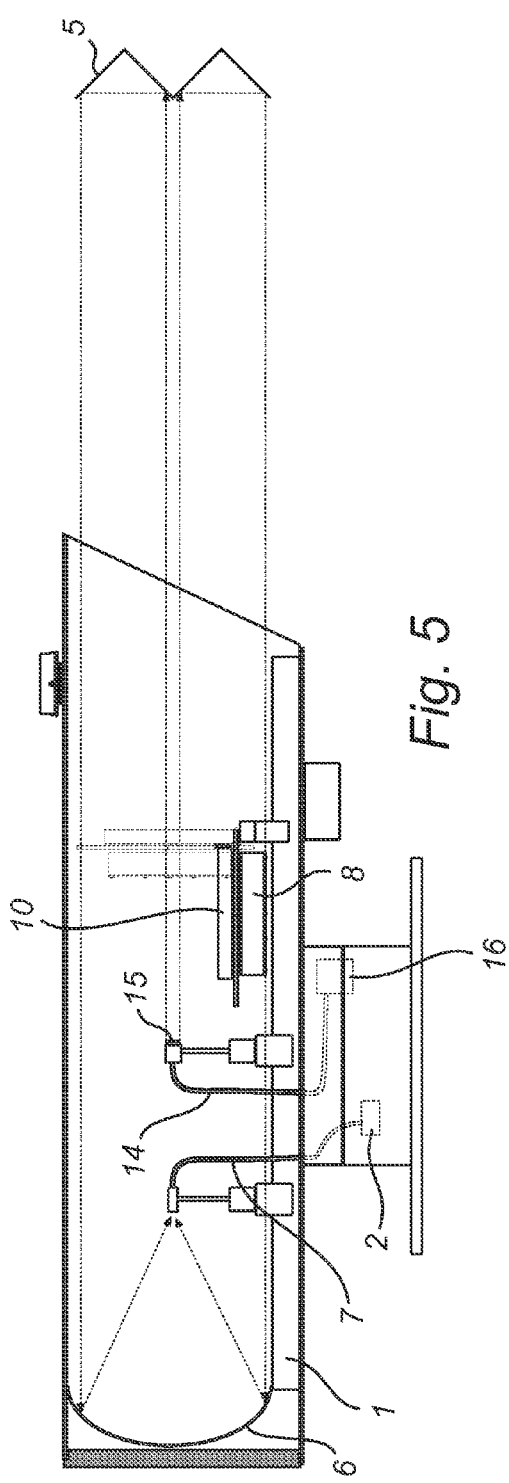

DEVICE FOR RADIATION ABSORPTION MEASUREMENTS AND METHOD FOR CALIBRATION THEREOF

TECHNICAL FIELD

The present invention relates generally to a device for radiation absorption measurements. More particularly, the present invention relates to an optical measurement device as defined in the introductory part of claim 1. The present invention also relates to a method for calibrating a device for radiation absorption measurements.

BACKGROUND ART

Optical measurement devices are commonly used for concentration measurements of gaseous substances. A number of different techniques, such as e.g. Differential Optical Absorption Spectroscopy (DOAS) applications, tuneable laser spectroscopy applications and Fourier transform spectroscopy, and corresponding measurement devices utilize radiation absorption by gas molecules for calculation or estimation of a certain molecular concentration along a radiation path, so called in sight absorption spectroscopy. The basic concept typically comprises a radiation source radiating a spectrally known electromagnetic radiation through a gas volume. Each gas molecule species in the volume will absorb the radiated photon energy according to its own unique absorption spectrum, determined by the discreet energy transitions possible in the particular molecule species (primarily dependent on electron, vibrational and rotational energy states for the particular molecule electrons). A spectrometer is typically used for determination of the spectrum of the radiation after possible absorption in the measurement volume. The measured spectrum is compared to the known spectrum of the radiation source and the unique absorption spectra for the gas species along the radiation path are identified. The concentration of a detected gas in the measurement volume is determined by the relative absorption measured for its spectrum according to the Beer-Lambert law. Absorption spectroscopy for gas analysis, as described above, is used in many applications for measurements of air pollution, such as general air pollution, exhaust gases from combustion engines, gaseous emissions from chimneys, volcanoes etc.. Commercially available measurement devices for these purposes usually comprise a telescopic device for transmitting light in a collimated way over a large distance. This can be accomplished by placing a light source in the focal point of a concave mirror or a lens to produce a substantially parallel beam of light. The collection of the light is made in a similar fashion by placing a detector in the focal point of a lens or a concave mirror.

EP 0 472 637 B1 shows a device for absorption measurements capable of both emitting and receiving light. The device is primarily made for measuring air pollution gases and is therefore often mounted on a chimney, a roof top or some other suitable outdoor location. The device has a light source positioned centrally in a tube. A concave mirror collimates the light in a forward direction towards a mirror positioned at a distance of 10 m to 10 km. The mirror redirects the light back into the tube, where another, bigger mirror placed behind the first concave mirror, focuses the light onto a detector faced backwards and positioned in the forward direction compared to the light source. A moveable shielding element is placed between the light source and the detector. During measurement, the shielding element is placed to block direct radiation from the light source to reach the detector. However, the shielding element can be folded away, while at the same time a second shielding element is placed to block the forward exit of the tube, so that the detector will only measure direct radiation from the light source. In that way reference measurements can be made of the light source and absolute concentration measurements of gas species can then be made.

WO90/04761 shows a similar device for absorption measurement, also for measuring air pollution. This device is also mounted in a pipe housing having a light source, a concave mirror at the back collimating the light from the light source forward towards a reflective mirror arranged at a distance from the light source. A second mirror is placed between the light source and the concave mirror with its reflective surface facing towards the concave mirror. A detector is placed between the second mirror and the concave mirror so that it is in the focal point of the concave mirror for light received by the device, while being shaded from the light source by the second mirror.

The above devices for air pollution measurements are delicate optical pieces of equipment placed in a rough outdoor environment. The rough environment implies that the devices fairly often have to be calibrated, aligned and maintained. A mirror might get dirty affecting its reflective spectrum. Aging of the detector, mirror and/or lenses might change the spectral behaviour of the device. Aging of the light source might alter the emitted radiation spectrum. The above mentioned problems will lead to a gradually decreased accuracy of the measurement results, while not necessarily affecting the precision of consecutive measurements. The latter makes the problem hard to discover. To be able to produce not only precise but also accurate measurement results maintenance of the equipment and recalibration of its spectral characteristics is necessary at a regular basis. The location of the measurement devices at for example industrial chimneys or rooftops makes the maintenance difficult, dangerous, time consuming and thus expensive.

SUMMARY OF THE INVENTION

It is an object of the present invention to improve the current state of the art, to solve the above problems, and to provide an improved device for electromagnetic radiation absorption measurements that is easier to calibrate regularly to compensate for the changes in the spectral behaviour of the device. More particularly, it is a preferred object of the present invention to provide an improved device for the measurement of air pollution, such as general air pollution, exhaust gases from combustion engines, gaseous emissions from chimneys, volcanoes etc. These and other objects are achieved by a device for radiation absorption measurements, comprising a radiation source emitting electromagnetic radiation having a wavelength in the interval 0.2 to 20 µm, a detector detecting said electromagnetic radiation, when in a measurement mode at least a portion of said radiation has passed through a medium and been reflected by a surface at a distance from said radiation source, before reaching said detector. The device is characterised in that said device further comprises a fluid calibration cell, which is adapted to be arranged in the path of the electromagnetic radiation between said radiation source and said detector.

To have a fluid calibration cell present in the optical measurement device makes it possible to recalibrate the device to adjust the absolute measurement values. If a mirror has become dirty or degraded by age so as to partly absorb a spectral part of the radiation signal a recalibration of the device can be made. By using the calibration cell filled with a fluid comprising a known concentration of a known substance a calibration of the absolute spectral response, i.e. the sensitivity of the device can be made. In this way the device is calibrated for accurate determination of the concentration of the fluid. A further advantage is that a spectral calibration of the detector, i.e. the spectral accuracy of the detector can be made using the known absorption spectrum of the fluid in the calibration cell. In this way the device is calibrated for accurate determination of the identity of the fluid.

According to a further embodiment of the invention the fluid calibration cell may be movable and adapted to be arranged, either in a first position, where said radiation passes through said fluid calibration cell before reaching said detector, or in a second, measurement mode position, where said radiation reaches said detector without passing through said fluid calibration cell.

By using a movable calibration cell the device can be made to automatically change from a measurement mode to a calibration mode where radiation has to pass the calibration cell to reach the detector. The above mentioned spectral calibration and calibration of sensitivity can then be made automatically and remote, reducing or avoiding dangerous and expensive maintenance of the device.

According to another embodiment of the present invention the device may further comprise a first reflective element directing said radiation from said radiation source through said fluid calibration cell to said detector.

The first reflective element will reflect radiation from the radiation source so that the radiation does not leave the housing of the measurement device. It s preferred that the first reflective element is a retro-reflector, to reflect the radiation 180°. If the fluid calibration cell is present in the radiation path absolute calibration of the device can be made with regard to sensitivity and spectral accuracy. If the fluid calibration cell is not present in the radiation path, the radiation from the radiation source will reach the detector without absorption. The latter will provide a reference calibration of the radiation source.

It is further preferred that said first reflective element may be movable and adapted to be arranged, either in a first position, wherein said radiation from said radiation source is directed through said fluid calibration cell before reaching said detector, or in a second position, wherein said radiation from said radiation source does not reach said first reflective element.

The possibility to move the reflective element away from the path of the radiation from the radiation source can be used to automatically perform calibration.

It is further preferred if the calibration cell according to the present invention further may comprise means for adding fluid to said fluid calibration cell and/or for removing fluid from said fluid calibration cell. This feature opens possibilities to exchange calibration fluid so that calibration can be made on different substances. The possibility to remove fluid from the calibration cell can be used either in the exchange process when switching to another calibration fluid, or for making absorption measurements with an empty calibration cell. Such a measurement can either be used to measure the absorption of the calibration cell as such, usually some kind of glass as e.g. quartz glass, or, if the absorption in the calibration cell material is neglected, for making a reference calibration of the radiation source.

It is further preferred that the fluid calibration cell may be filled with a gas comprising at least one of the substances chosen from the group consisting of $Br_2$, $CHN$, $Cl_2$, $ClO_2$, $CO$, $CO_2$, $COCl_2$, $CS_2$, $H_2O$, $H_2S$, $HBr$, $HCl$, $HCN$, $HF$, $Hg$, $HNO_2$, $N_2O$, $NH_3$, $NO$, $NO_2$, $NO_3$, $O_2$, $O_3$, $SO_2$, $SO_3$, $C_{10}H_8$, $C_2H_2$, $C_2H_4$, $C_2H_4O$, $C_2H_6$, $C_2H_6O$, $C_3H_8$, $C_6H_3(CH_3)_3$, $C_6H_4(CH_3)_2$, $C_6H_5C_2H_5$, $C_6H_5CH=CH_2$, $C_6H_5OH$, $C_6H_6$, $C_7H_8$, $CH_2O$, $CH_3C_2H_4OH$, $CH_4$, $CH_4O$. The gas or gasses used for calibration can preferably be changed automatically by using containers storing the gas(es) and having means such as pipes and electrical valves communicating with the calibration cell.

According to one embodiment of the present invention, the device may further comprise a collective element collecting said radiation onto said detector. The collective element preferably has a focal point, said detector being located at said focal point. The collective element is used to enlarge the collecting surface exposed to incident radiation during measurements. The radiation is focused onto the usually small detector to increase the signal detected by the detector. It should however be noted that when the radiation source is well collimated, as e.g. in the case of a laser radiation source, the device could be used without a collecting element. It is also feasible to increase the detector surface instead of using collecting optics.

The device according to the invention preferably further comprises transmitting means transmitting said radiation to said detector. The transmitting means can for example be a system of one or more mirrors or an optical fibre used to transport the collected radiation to the detector. The detector can then be placed at a distance from the normal radiation path.

It is further preferred that the device according to the present invention comprises a directing element for directing said radiation emitted from said radiation source. The directing element preferably has a focal point, said radiation source being located at said focal point, such that said emitted radiation from said radiation source is directed substantially spatially coherent. When using an incandescent radiation source, a gas discharge radiation source or a LED radiation source, radiation is radiated in all directions. A directing element that collimates the radiation to form a substantially parallel beam of radiation is then desirable to be able to collect the radiation at a long distance. The collecting element could be a lens or concave mirror or any other optical component able to focus electromagnetic radiation.

According to one embodiment of the invention the device may further comprise a second reflective element arranged at a distance from said radiation source such that radiation from said radiation source is redirected substantially 180°. The second reflective element is preferably a retro-reflector. The reflector is preferably placed at a distance of up to 10 km from the radiation source. The length of the radiation path from the radiation source to the detector will thus be double the distance between the radiation source and the second reflective element. A long path length is important e.g. when measuring low concentrations of a substance in a target gas, as is the case when measuring air pollution.

The detector in the device preferably includes at least an element chosen from the group consisting of a photodiode, a spectrometer, and a photo multiplier tube. The radiation source is preferably chosen from the group consisting of a xenon lamp, a LED-lamp, a laser, a tungsten lamp and a mercury lamp.

The present invention further relates to a method for calibrating a device for radiation absorption measurements, comprising the steps of: emitting electromagnetic radiation having a wavelength in the interval 0.2 to 20 µm, directing at least a portion of said electromagnetic radiation through a fluid calibration cell, and detecting said electromagnetic radiation.

It is preferred that a reference calibration of said radiation source is made when said fluid calibration cell is evacuated.

It is further preferred that the method comprises the steps of adding fluid to said fluid calibration cell, and/or removing fluid from said fluid calibration cell.

The method for calibrating the device further includes the use of the device according to the above description.

It should be noted that the inventive method may incorporate any of the features described above in association of the inventive device and has the same corresponding advantages.

A typical calibration scheme using the device according to the present invention could firstly be to introduce the first reflective element, keeping the calibration fluid cell away from the radiation path, and thus making a reference calibration of the radiation source emission spectrum ($I_0$) by measuring the intensity (I) of the detected light. Secondly, the calibration cell, filled with a calibration gas, is introduced in the radiation path, the first reflective element still being in place as in the first step. A spectrum ($I_1'$) of the radiation is measured with absorption from the calibration gas and possibly also a small absorption by the calibration cell material, most probably glass of some kind, preferably quartz glass. Thirdly, the gas is evacuated from the calibration cell allowing for measurements of the radiation spectrum ($I_0'$) only subjected to the absorption by the calibration cell alone. The true transmitted intensity of the calibration gas spectrum can be calculated as $I_1=I_1'+(I_0-I_0')$. According the Beer-Lambert law the absorption can be calculated as follows: $A=\ln(I_0/I_1) = \epsilon \cdot L \cdot c$, where $\epsilon$ is absorption cross section of the species, L is the absorbing length and c is the concentration of the species. Having a known concentration of the gas in the fluid calibration cell, the absorption cross section can thus be calculated.

BRIEF DESCRIPTION OF THE DRAWINGS

The above objects, as well as additional objects, features and advantages of the present invention, will be more fully appreciated by reference to the following illustrative and non-limiting detailed description of preferred embodiments of the present invention, when taken in conjunction with the accompanying drawings, wherein:

FIG. 2a is a cross-section profile of the transmitted light from the device in FIG. 1;

FIG. 2b is a cross-section profile of the detected light;

FIG. 3a is a schematic drawing of the moveable fluid calibration cell and the moveable reflective element of FIGS. 1, 4 and 5, where only the reflective element is introduced in the radiation path;

FIG. 3b is a schematic drawing of the moveable fluid calibration cell and the moveable reflecting element of FIGS. 1, 4 and 5, where both the reflective element and the fluid calibration cell are introduced in the radiation path;

FIG. 3c is a schematic drawing of the moveable fluid calibration cell and the moveable reflective element of FIGS. 1, 4 and 5, where neither the reflective element nor the fluid calibration cell are introduced in the radiation path;

FIG. 4 is a schematic drawing of a first alternative embodiment of the present invention, where the fluid calibration cell and the reflective element are placed at a different position compared to FIG. 1; and FIG. 5 is a schematic drawing of a second alternative embodiment of the present invention.

DETAILED DESCRIPTION OF PREFERRED EMBODIMENTS OF THE INVENTION

Figure 1:
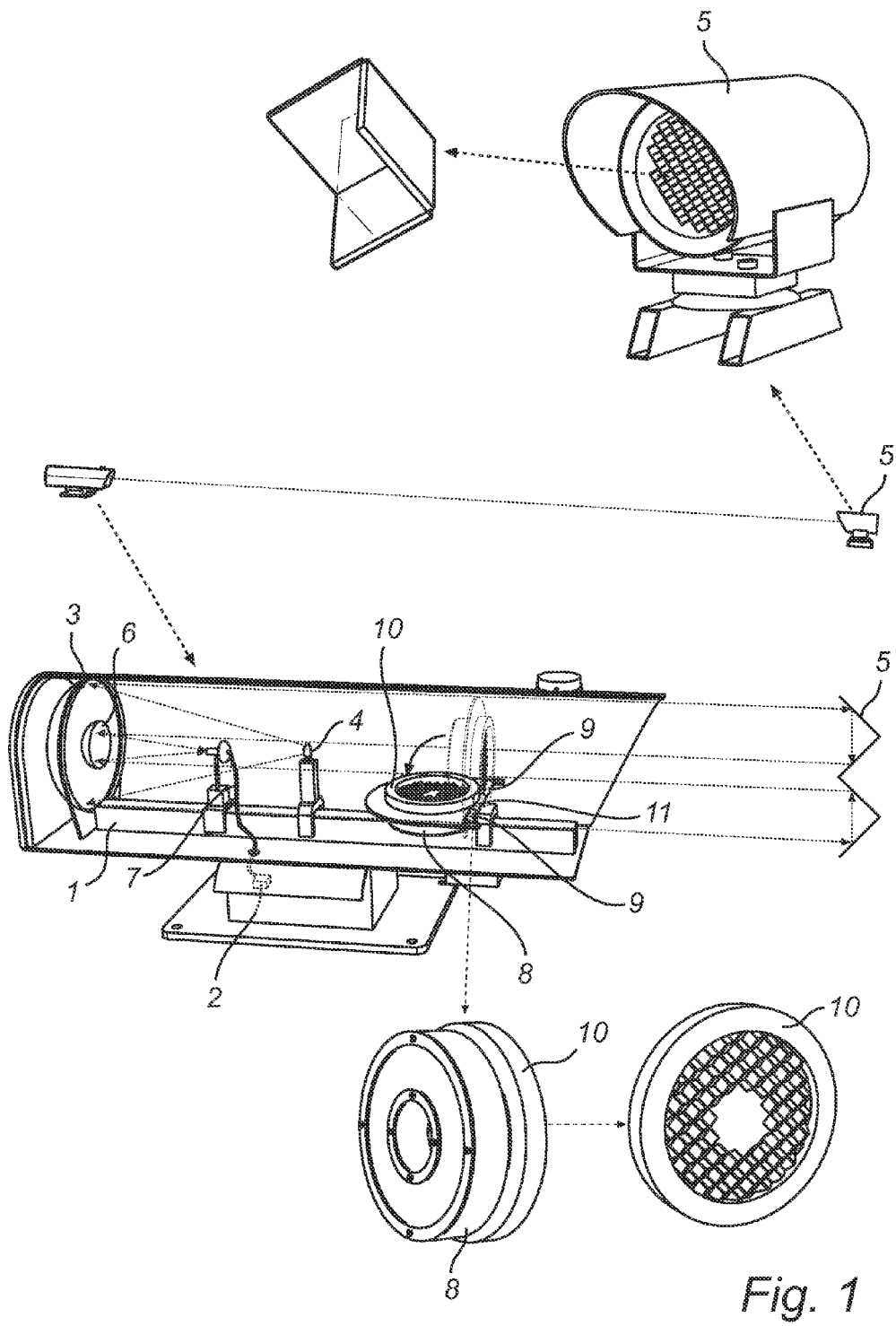
FIG. 1 is a schematic drawing of a preferred embodiment of the present invention.

FIG. 1 shows a preferred embodiment of a device for radiation absorption measurements according to the present invention. The device is built on a solid optical bench 1. A directing element 3, in the form of a large concave mirror, is placed at the back (left) of the optical bench 1, to direct radiation from the radiation source 4. The radiation source 4 is placed in the focal point of the directing element 3 so that the radiation from the radiation source 4 after reflection by the directing element 3 will be directed substantially spatial coherent as a parallel beam of radiation. A second reflective element 5 is placed at a distance up to 10 km from the radiation source. The second reflective element 5 is a retro-reflector, an optical component designed to reflect incident radiation substantially 180° with little or no influence of the incident angle of the incident radiation. A collective element 6 in the form of a concave mirror is placed in front of (to the right of) the directing element 3. A transmitting means 7 is placed in the focal point of the collective element 6 to lead the radiation to a detector 2, for example a spectrometer. The transmitting means 7 is preferably an optical fibre, but could also be a mirror arrangement or any other transmitting arrangement to direct the radiation to the detector 2. A moveable fluid calibration cell 8 is placed in front of (to the right of) the radiation source 4. In this embodiment the fluid calibration cell 8 is a cylindrical cell having a hole in the middle. The fluid calibration cell 8 is pivotable around a hinge 9 (see FIG. 3a) and is in FIG. 1 folded down to not disturb the radiation path of the measurement device. Adjacent the fluid calibration cell 8 is a first reflective element 10 which is also pivotably hinged on a hinge 11 (see FIG. 3c) and folded down in FIG. 1 not to disturb the radiation path.

FIG. 1 further has an enlargement of the fluid calibration cell 8 and the first reflective element 10. In the embodiment shown in FIG. 4 it is preferred, to use a ring-shaped fluid calibration cell 8, since the shading from the optical fibre 7 and the collective element 6 generates a ring-shaped transmitted radiation profile. It is however possible, in an embodiment as shown in FIG. 1, to use a fluid calibration cell that is cylinder-shaped without a hole in the central part of the cylinder or shaped in basically any form. The fluid calibration cell 8 is preferably made of a material that is transparent to the wavelengths that are emitted from the radiation source and that are of interest for the measurement. Glass, preferably quartz glass of good quality, is an example of such a material. The fluid calibration cell 8 is preferably equipped with a means to introduce and remove fluid (not shown) to and from the fluid calibration cell 8. The cell 8 could, however also be pre-filled with one gas, preferably the gas of interest for the gas concentration measurement. The first reflective element 10 can be a retro-reflecting assembly made of a plurality of retro-reflecting mirrors, a plane mirror, a slightly concave mirror, or a slightly convex mirror, depending on how the radiation is collected in the device. In the embodiment of FIG. 1 and FIG. 4, the first reflective element 10 is preferably slightly focusing, e.g. a concave mirror and in the embodiment of FIG. 5, the first reflective element 10 is preferably plane or slightly convex. The first reflective element 10 can also be ring-shaped for the same reasons as for the fluid calibration cell 8.

FIG. 2a shows a transmitted radiation profile 12 from the device of FIG. 1. In FIG. 1 it can be seen that the optical fibre assembly blocks the radiation from the radiation source 4 so that it does not reach the collective element 6. This leads to a hole in the transmitted radiation profile, presenting a ring-shaped profile.

FIG. 2b shows the received radiation profile 13 of the radiation as reflected by the collective element 6 in FIG. 1.

FIG. 3a shows the fluid calibration cell 8, pivotable around the hinge 9, in a down-folded position. The first reflective element 10, pivotable around the hinge 11, is in its up-right position, i.e. introduced in the radiation path of the device according to FIG. 1. The first reflective element 10 will reflect the radiation from the radiation source 4 so that it does not leave the measurement device. Instead the radiation will be reflected back to the collective element 6 and focused onto the detector 2 via the optical fibre 7. The radiation collected by the detector 2 will thus not be subjected to absorption by fluids, such as e.g. pollution gases, outside the calibration device. In FIG. 3b, both the fluid calibration cell 8, and the first reflective element 10 are in their up-right positions, i.e. introduced in the radiation path of the device according to FIG. 1. The radiation from the radiation source 4 will thus be reflected in the same manner as in FIG. 3a, with the addition of the fluid calibration cell 8 being placed in the radiation path so that the radiation will pass the cell 8 twice. In FIG. 3c both the fluid calibration cell 8 and the first reflective element 10 are in their down-folded position so as not to affect the radiation measurement path. With reference to both FIGS. 1 and 3c the radiation from the radiation source 4 is thus directed via the directing element 3 to the distant second reflective element 5, where the radiation is reflected back to the collective element 6, where it is focused onto the transmitting means 7, leading the radiation to the detector 2.

FIG. 4 shows an alternative embodiment of the present invention. The embodiment is similar to that shown in FIG. 1 with the exception that the fluid calibration cell 8 and the first reflective element 10 are arranged between the radiation source 4 and the optical fibre 7, near the radiation source. Due to the ring-shape of the fluid calibration cell 8 and the first reflective element 10, the light source can emit light to the directing element 3 via the holes in the fluid calibration cell 8 and the first reflective element 10, also when these elements are in their up-right position. The directing element 3 will direct the radiation onto the first reflective element 10 and the first reflective element 10 will reflect the radiation onto the collective element 6, the transmitting element 7 and thus onto the detector 2. When the device is in measurement mode, the fluid calibration cell 8 and the first reflecting element are folded down to not disturb the radiation path in the measurement.

FIG. 5 shows a second alternative embodiment of the invention where the radiation from a radiation source 16 is lead to the device via a second transmitting means 14. The second transmitting means 14 is preferably an optical fibre, but it could also be a mirror arrangement. A directing element 15, in this embodiment a collimating lens, is placed at a proper location in relation to the fibre to collimate the radiation from the optical fibre in the direction of the distant second reflective element 5. A collective element 6 is arranged at the back of the optical bench 1 to collect the light onto the detector 2 via the transmitting means 7 in the same manner as in the embodiments of FIGS. 1 and 4. The collective element 6 can however be made larger, because of the absence of the directing element 3 of the embodiments of FIGS. 1 and 4.

It should be noted that a number of other possible embodiments are possible for emission and collection of the radiation according to the present invention. The directing element 3, 15 could be arranged at other positions and could be focal optics as concave mirrors, lenses, etc. Also the collective element 6 could be a focusing lens instead of a collecting mirror. The collective element 6 could also be neglected if the detector 2 and/or the transmitting element has a large surface area; if the detector 2 is very sensitive; if the collected radiation is very strong; or if the collected radiation is very well collimated as is possible with e.g. laser radiation.

The calibration of the device according to the invention will now be described with reference to FIGS. 1, 4, 5 and FIGS. 3a to 3c. After a predetermined time or if the measurement values indicate a possible disturbance in accuracy of the measurements, the device can automatically initiate a calibration sequence. The device will then raise the first reflective element 10 (FIG. 3a), preferably by using an electrical step motor, to reflect the radiation from the radiation source 4 back to the detector 2. To avoid disturbance from substances in the environment in case of large concentrations thereof in the ambient atmosphere, the device housing (not shown) can optionally be flushed with a gas species without absorption in the spectral range of interest and a small overpressure can be established to keep outside gases outside the device housing. A calibration of the absolute spectral values ($I_0$) of the radiation source including the function of the device can then be recorded since, all optical components normally used in the measurement device are also used in the calibration measurement. The measured transmission spectrum ($I_0$) is saved and can be used in later calibration steps and in the real absolute concentration measurements. Next the fluid calibration cell 8 is raised to its up-right position (FIG. 3b), preferably by use of a second electrical step motor, while keeping the first reflective element in its up-right position. If the absorption of the calibration cell material is not negligible a spectrum of the transmission through the cell ($I_0'$) is recorded using an evacuated fluid calibration cell 8 or having it filled with a species not absorbing in the spectral range of interest. The fluid calibration cell 8 is then filled with a known concentration of calibration gas and a spectrum of the transmission ($I_1'$) is recorded. The transmission through the calibration cell can be calculated by $I_1=I_1'+(I_0-I_0')$. This can be repeated for all species of interest. If the absorption of the fluid calibration cell material is found negligible, i.e. $I_0=I_0'$, and only one species is of interest in the concentration measurements, a prefilled calibration cell can be used, having a known concentration. The absorption cross section for each calibration species can then be calculated according to the Beer-Lambert Law.

When the calibration sequence is completed the fluid calibration cell 8 and the first reflective element 10 are folded down to not disturb the radiation path during real measurements (FIG. 3c). The previously calculated cross section is used to calculate the concentration of gases in a measurement path by measuring the absorption in the measurement path and by using the Beer-Lambert law with the calibrated value of absorption cross section for each species of interest.

It should also be noted that a spectral calibration of the detector 2, commonly a spectrometer, can be made using a known calibration gas or known gases. Also this calibration can of course be automated and scheduled since the fluid calibration cell always is present in the measurement device.

It is understood that other variations in the present invention are contemplated and in some instances, some features of the invention can be employed without a corresponding use of other features. Accordingly, it is appropriate that the appended claims be construed broadly in a manner consistent with the scope of the invention.

The invention claimed is:

1. A device for radiation absorption measurements, the device comprising:
   a radiation source emitting electromagnetic radiation having a wavelength in the interval 0.2 μm-20 μm;
   a detector detecting the electromagnetic radiation, when in a measurement mode at least a portion of the electromagnetic radiation has passed through a medium and been reflected by a surface at a distance from the radiation source, before reaching the detector; and a fluid calibration cell, which is adapted to be arranged in the path of the electromagnetic radiation between the radiation source and the detector;

wherein the fluid calibration cell is movable into a first position, wherein the electromagnetic radiation passes through the fluid calibration cell before reaching the detector, and a second, measurement mode position, wherein the electromagnetic radiation reaches the detector without passing through the fluid calibration cell.

2. The device according to claim 1, further comprising a first reflective element directing the electromagnetic radiation from the radiation source through the fluid calibration cell to the detector.

3. The device according to claim 2, wherein the first reflective element is movable into a first position, wherein the electromagnetic radiation from the radiation source is directed through the fluid calibration cell before reaching the detector, and a second position, wherein the electromagnetic radiation from the radiation source does not reach the first reflective element.

4. The device according to claim 1, further comprising means for at least one of adding fluid to the fluid calibration cell and removing fluid from the fluid calibration cell.

5. The device according to claim 1, further comprising a collective element collecting the electromagnetic radiation onto the detector.

6. The device according to claim 5, wherein the collective element has a focal point; and wherein the detector is located at the focal point.

7. The device according to claim 1, further comprising transmitting means for transmitting the electromagnetic radiation to the detector.

8. The device according to claim 1, further comprising a directing element to direct the electromagnetic radiation emitted from the radiation source.

9. The device according to claim 8, wherein the directing element has a focal point; and wherein the radiation source is located at the focal point, such that the emitted electromagnetic radiation from the radiation source is directed substantially spatially coherent.

10. The device according to claim 1, further comprising a second reflective element arranged at a distance from the radiation source such that the electromagnetic radiation from the radiation source is redirected substantially 180°.

11. The device according to claim 10, wherein the second reflective element is a retro-reflector.

12. A method for calibrating a device for radiation absorption measurements, the method comprising:

emitting electromagnetic radiation having a wavelength in the interval 0.2 μm-20 μm;

directing at least a portion of the electromagnetic radiation through a fluid calibration cell;

detecting the electromagnetic radiation; and making a reference calibration of the radiation source when the fluid calibration cell is evacuated.

13. The method according to claim 12, further comprising at least one of adding fluid to the fluid calibration cell; and removing fluid from the fluid calibration cell.

* * * * *